United States Patent [19]
Aspel

[11] Patent Number: 5,538,421
[45] Date of Patent: Jul. 23, 1996

[54] DENTAL INSTRUMENT

[76] Inventor: Thomas E. Aspel, 3149 Old Post Rd., Fallbrook, Calif. 92028

[21] Appl. No.: 311,883

[22] Filed: Sep. 26, 1994

Related U.S. Application Data

[63] Continuation-in-part of Ser. No. 93,096, Jul. 16, 1993, abandoned.

[51] Int. Cl.[6] .................................................. A61C 7/00
[52] U.S. Cl. ................................................ 433/4; 433/159
[58] Field of Search ................................ 433/4, 153, 157, 433/159

[56] References Cited

U.S. PATENT DOCUMENTS

| 491,932 | 2/1893 | Whitlock | 433/159 |
|---|---|---|---|
| 536,166 | 3/1895 | Angle . | |
| 882,404 | 3/1908 | Miner . | |
| 1,177,223 | 3/1916 | Angle . | |
| 1,304,720 | 5/1919 | Young . | |
| 1,346,584 | 7/1920 | Angle . | |
| 1,594,143 | 7/1926 | Angle et al. . | |
| 1,670,361 | 5/1928 | Johnson . | |
| 2,985,962 | 5/1961 | Shiner | 433/4 |
| 3,146,804 | 9/1964 | Wallshein | 140/106 |
| 3,755,902 | 9/1973 | Northcutt . | |
| 3,911,583 | 10/1975 | Hoffman | 433/4 |
| 3,986,265 | 10/1976 | Cusato | 433/4 |
| 4,035,919 | 7/1977 | Cusato . | |
| 4,184,259 | 1/1980 | Sosnay | 433/4 |
| 4,385,890 | 5/1983 | Klein | 433/4 |
| 4,600,381 | 7/1986 | Hodgson | 433/4 |
| 4,752,220 | 6/1988 | Dietrich | 433/1 |
| 4,900,251 | 2/1990 | Andreasen | 433/20 |

OTHER PUBLICATIONS

Masel, Product Catalog, 1993 with particular reference to pp. 4, 5.
ETM Corporation, Product Catalog, Undated with particular reference to pp. 8, 9, 12, 13, 19, 20, 22, 26. Product Sheet, Undated.

Primary Examiner—Cary E. O'Connor
Attorney, Agent, or Firm—Frank J. McGue

[57] ABSTRACT

A dental instrument is provided comprising a first member having a first handle opposite a first jaw and a second member having a second handle and a second jaw. The first jaw is longer than the second jaw, and both jaws have inner surfaces. The first member is pivotally connected to the second member such that the first handle opposes the second handle and the first jaw opposes the second jaw. Movement of the first handle and the second handle correspondingly cause movement of the first jaw and the second jaw. The inner surface of one of the jaws is disposed within an acute angle of the centerline of the instrument. The inner surface of the other jaw is disposed at the acute angle from the disposed jaw.

14 Claims, 3 Drawing Sheets

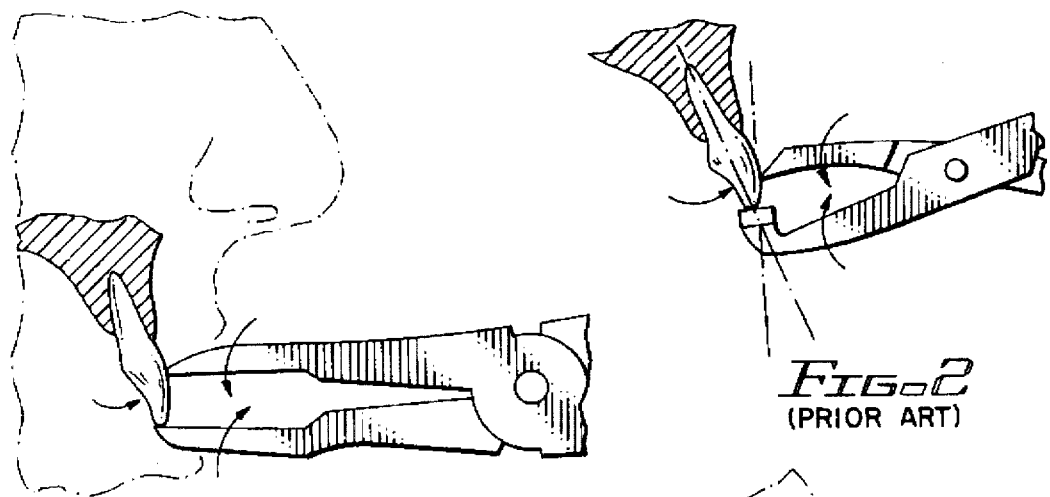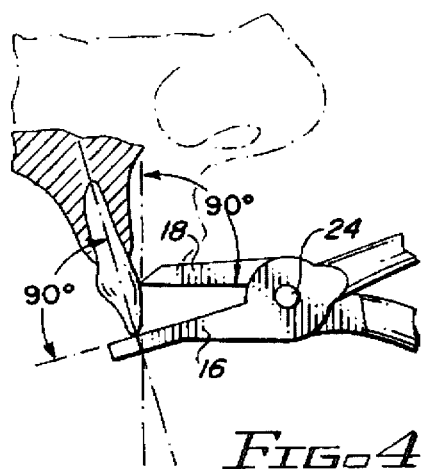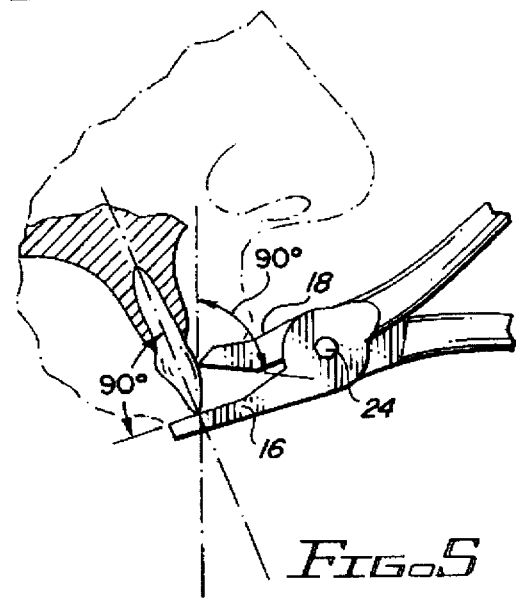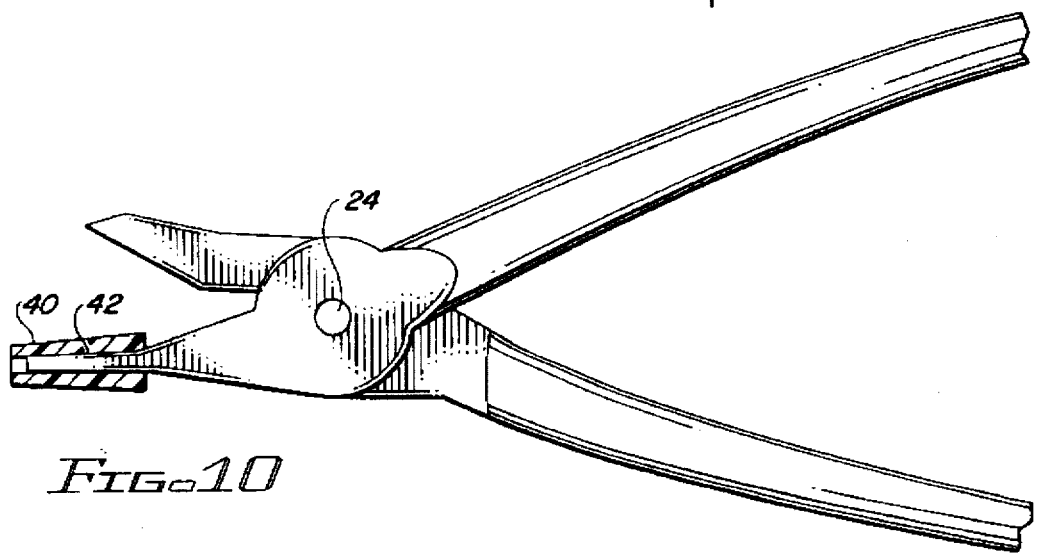

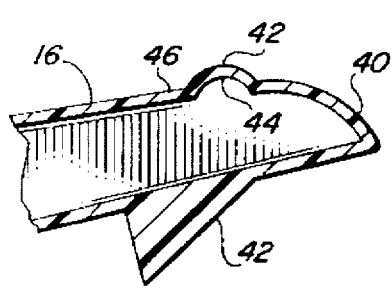
FIG. 9
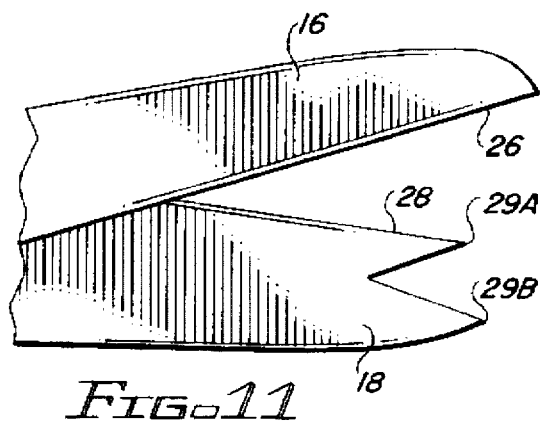
FIG. 11
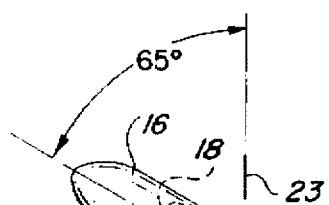
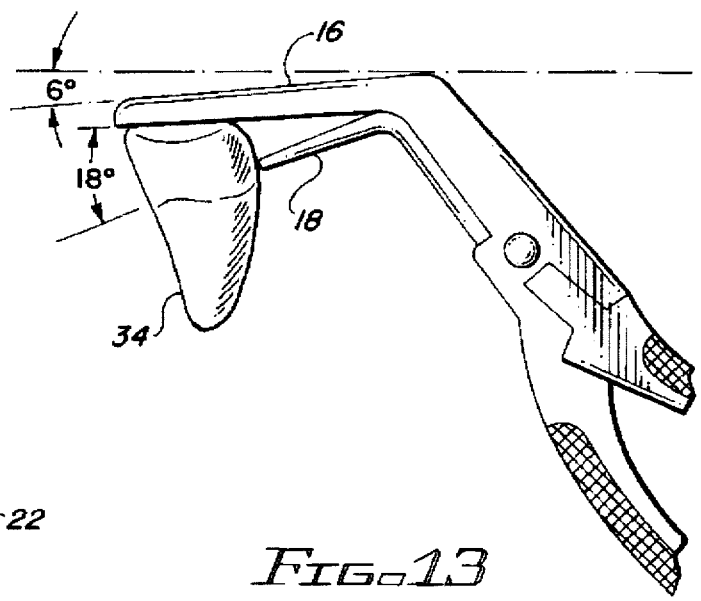
FIG. 12
FIG. 13

DENTAL INSTRUMENT

RELATED APPLICATION

This is a continuation-in-part of application Ser. No. 08/093,096 filed on Jul. 16, 1993, now abandoned.

FIELD OF INVENTION

The invention relates to dental appliances and, in particular, to dental appliances used to remove orthodontic braces, bands, brackets and bonding materials from tooth surfaces.

DESCRIPTION OF THE RELATED ART

In dentistry, and specifically in the branch of dentistry dealing with the correction of irregularities of the teeth called orthodontics, often brackets, bands, buttons, cleats, and braces (collectively "attachments") are placed on the teeth of a patient to correct irregularities. To secure such attachments to the patient, various cements are used to bond the attachments to the tooth enamel. Examples of commercially available bonding materials are Zincoxyphosphates, i.e., Calk, and Ames Cements; Duralon, Hypoxcements, and composites such as Durabond, Concise, and Unitec Corp.'s Transbond.

These cements are designed to hold the attachments in place under the rigorous conditions found in a typical human mouth. For example, the simple act of chewing will exert a great deal of force on cemented attachments. In addition, the harsh chemical environment of a mouth often includes digestive chemicals found in saliva, acidic and basic compounds found in various foods, cleaning compounds present in toothpastes, and the like. Cements capable of withstanding such an environment without losing cohesive strength are typically very strong and virtually inert, after setting, to chemicals found in the human mouth.

Thus, at the end of the prescribed course of orthodontic treatment, removal of such attachments and the associated cement is a difficult problem. To solve the problem, various tools have been designed to forcibly remove the orthodontic attachments.

Currently known devices for removing orthodontic appliances are plier-like in that they consist of two members, each member having a handle and a jaw opposite the handle. The two members are attached by a pivot such that the respective jaws and the respective handles are opposite each other. When the handles are brought together by a user, the jaws also are brought together by way of a pivotal movement.

In general, in known devices, one jaw is longer than the other jaw. The longer jaw is designed to provide a fulcrum by resting upon the occlusal (biting) surfaces of a tooth while the shorter jaw will scrape the side of primarily the facial (front teeth on the lip side) and buccal (cheek side) surfaces of the teeth to chip away cement and engage the orthodontic attachments for removal. The longer jaw is often equipped with a plastic button to protect the biting surface from chipping. The buttons may become worn or damaged after prolonged use but are not easily removable or replaceable.

The buccal surfaces and facial surfaces are somewhat curved in the gingival (gum) to occlusal (biting) surface direction. However, when viewed as a surface drawn gingivally-occlusally (from the gum towards the biting surface) at the mid-mesial distal point (roughly halfway between the gum and the biting surface), the surface will represent a relatively flat plane. It is in this area of the tooth that most attachments are bonded and thus it is this area where the orthodontial pliers are often used.

However, the presently known pliers are not ideally designed to prevent tipping (or luxation) of the tooth in use. Such tipping or luxation of the tooth will result in pain caused by compression of the periodontal ligament and bone around the tooth. The periodontal ligament contains nerve and blood supply to the tooth and contains the periodontal fibers which make up the ligamentous attachment of the tooth to the bone and gums. The ligamentous attachment with the nerve and blood supply is in a very contained area and is positioned primarily to accept force through the longitudinal axis or centerline of the tooth, i.e. biting or clenching will not cause pain or discomfort.

In all present known designs, when the cutting edge of the second jaw is positioned to remove cementing material or attachments, the first jaw is positioned on the biting surface. When the plier is closed, a vector of force is created that tips or luxates the tooth buccally or facially, compressing the peridontal ligament between the root and bone, causing pain.

For example, as best seen in FIG. 1, one presently known design is disclosed in U.S. Pat. No. 4,752,220 which issued to Dietrich on Jun. 21, 1988. A second example of a current design is seen in FIG. 2 which illustrates generally designs found in a product catalog of the ETM Corporation. Closing the jaws of Dietrich or the ETM product to scrape the cement and/or attachments off of the tooth will result in a tipping of the tooth forward in the jaw. That tipping will cause pain to the patient.

Thus, there is a need for a dental instrument which directs the first jaw force vector downwardly along the longitudinal axis of the tooth while at the same time the second jaw force vector is directed parallel to the tooth's surface in a working or scraping position. A tool is needed which is useful in the confined spaces in the patient's mouth. Further, the tool is needed which is useful in both removal of attachments or appliances and for scraping the remaining bonding materials from a tooth.

The present invention overcomes the shortcomings associated with the existing devices.

SUMMARY OF THE INVENTION

In accordance with one aspect of the present invention, a dental appliance useful for removing attachments and cements from a tooth is provided comprising a first member having a first handle opposite a first jaw, and a second member having a second handle and a second jaw. The first jaw is suitably longer than the second jaw, and both jaws have inner surfaces. In accordance with a preferred embodiment, the first member is advantageously pivotally connected to the second member such that moving the first handle and the second handle from an open position to a closed position correspondingly causes the jaws to move from an open position to a closed position. The inner surface of one of the first or second jaws is radially disposed from the pivot, while the inner surface of the other jaw is disposed at an acute angle from the inner surface of the radially disposed jaw. This orientation of the jaws directs force exerted by the first jaw downwardly substantially along the longitudinal axis of the tooth, thus minimizing discomfort to the patient. Also, the force exerted by the handles to the second jaw is efficiently directed parallel to the surface of tooth.

BRIEF DESCRIPTION OF THE DRAWINGS

A preferred exemplary embodiment of the present invention will hereinafter be described in conjunction with the appended drawing figures, wherein like designations denote like elements, and:

FIG. 1 is a side view of a plier of the prior art being used on a tooth;

FIG. 2 is a side view of another plier of the prior art being used on a tooth;

FIG. 4 is a side view of one exemplary embodiment of the present invention being used on a tooth;

FIG. 5 is a side view of an alternate exemplary embodiment of the present invention being used on a tooth;

FIG. 9 is a close up side view of an exemplary embodiment of orthodontic pliers having a disposable sheath in accordance with the present invention;

FIG. 10 is a side view of an alternate exemplary embodiment of orthodontic pliers having a disposable sheath in accordance with the present invention;

FIG. 11 is a side view of an alternate exemplary embodiment of orthodontic pliers in accordance with the present invention; and FIG. 12 is a top view of an alternate exemplary embodiment of orthodontic pliers in accordance with the present invention;

FIG. 13 is a perspective view of the embodiment of FIG. 12.

DETAILED DESCRIPTION OF THE PREFERRED EMBODIMENT

Figure 3:
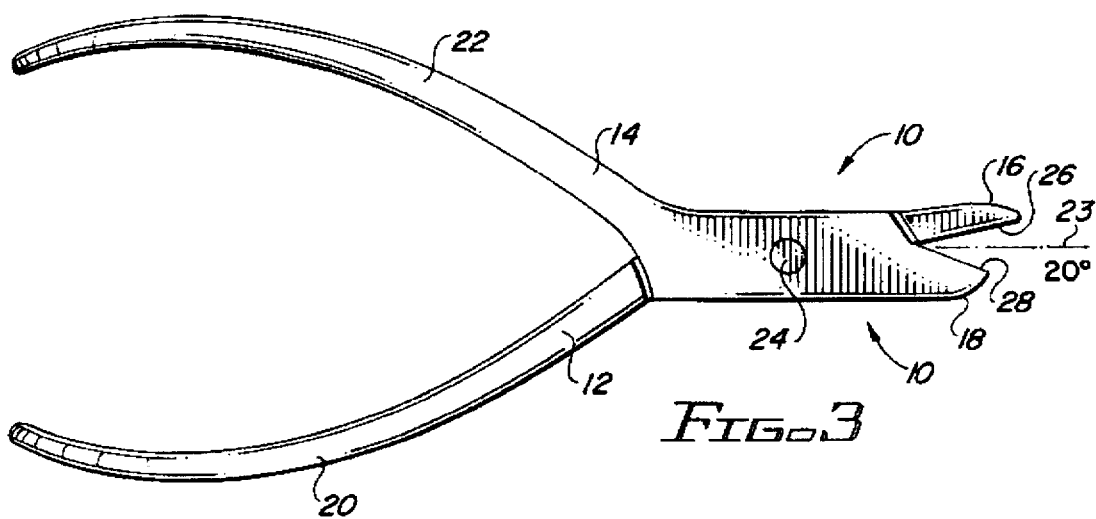
FIG. 3 is a side view of an exemplary embodiment of orthodontic pliers in accordance with the present invention.

Referring to FIG. 3, an instrument 10 in accordance with the present invention comprises a first member 12 and a second member 14. First member 12 includes a jaw 16 disposed at one end thereof and a handle 20 disposed at the other end. Second member 14 includes a jaw 18 disposed at one end thereof and a handle 22 disposed at the other end.

First member 12 and second member 14 are suitably joined at a pivot 24 whereby respective jaws 16, 18 oppose each other such that force exerted on handles 20, 22 draws jaws 16, 18 toward one another. A centerline 23 of instrument 10 is an imaginary line which extends through pivot 24 and the point where jaws 16 and 18 meet.

Instrument 10 is preferably manufactured from stainless steel, but can be made from any suitable material having sufficient strength to remove the orthodontic attachments and able to withstand sterilization, i.e., an autoclave or high heat. Alternatively, a disposable version may be used, thus eliminating the need for an ability to withstand sterilization.

First jaw 16 is suitably longer than second jaw 18 by an amount sufficient to allow first jaw 16 to engage the biting surface of a tooth while second jaw 18 scrapes the side of the tooth. In a preferred embodiment, first jaw 16 is longer than second jaw 18 by about four to ten millimeters (4–10 mm), most preferably by about six to seven millimeters (6–7 mm). The length of the respective jaws 16 and 18 is measured from pivot 24 to the distal tip of the jaw.

As best seen in FIG. 3, first jaw 16 advantageously comprises an inner surface 26 which is preferably oriented radially from pivot 24, i.e., inner surface 26 is suitably disposed substantially parallel to an imaginary line extending from pivot 24 to the point on inner surface 26 that contacts the surface of the tooth. Thus, during use, the force exerted by first law 16 through pivot 24 is generally directed along a line perpendicular to inner surface 26 in the illustrated embodiment. Consequently, to the extent inner surface 26 is held perpendicular to the longitudinal axis of the tooth, a substantial component of the force exerted by first jaw 16 as respective handles 20, 22 are urged together will be generally directed downwardly along the longitudinal axis of the tooth.

Second jaw 18 suitably comprises an inner surface 28 which opposes inner surface 26 of first jaw 16. Inner surface 28 is advantageously disposed at an acute angle with respect to inner surface 26 when instrument 10 is in the working position. In the context of the illustrated embodiment, the term "working position" refers to the position wherein first jaw 16 is positioned on the biting surface of a tooth such that second jaw 18 may be conveniently manipulated by the user to engage the hardened cement to be scraped off or the orthodontic appliance to be removed. In a typical mouth, that position is when cutting edge 29 of jaw 18 is separated from jaw 16 by between four to nine millimeters, most commonly by about 6.5 mm; at that point, jaws 16 and 18 are disposed from each other at an angle between 10° to 40°, preferably about 15° to 28° most preferably about 22°, from each other.

In an alternative embodiment of the present invention, inner surface 28 of second jaw 18 may be radially disposed with respect to pivot 24 and inner surface 26 of first jaw 16 may be disposed at an acute angle with respect to surface 28 when instrument 10 is in the working position. Instrument 10 will adequately function in either embodiment. In other embodiments best seen in FIGS. 4 and 5, respective surface 26 and 28 are oriented with respect to each other by working angles in the range of about 10° to 40°, preferably about 15° to 28°, and most preferably about 22°. In addition, inner surfaces 26, 28 of jaws 16, 18, respectively, are oriented between about 0° and 40°, most preferably between about 0° and 22° to the centerline 23 of the tool.

Figure 6:
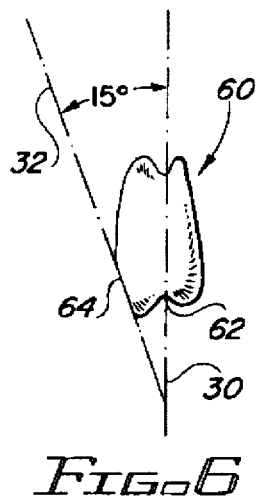
FIG. 6 is a side view of an upper bicuspid tooth.

Referring now to FIG. 6, illustrated is a profile of a representative upper bicuspid tooth 60 as measured proximate to the pivot. Upper bicuspid tooth 60 is found in the upper (maxillary) jaw of a typical human mouth. Upper bicuspid tooth 60 has a biting surface 62, a facial surface 64, a longitudinal axis 30, and a line 32 tangent to facial surface 64. The angle made between longitudinal axis 30 and line 32 in this particular tooth is about 15°.

The prevent inventor has determined that the perfect working angle between respective surfaces 26 and 28 for working on upper bicuspid tooth 60 is preferably approximately equal to the 15° angle between axis 30 and line 32. At that angle, inner surface 26 is preferably oriented perpendicular to longitudinal axis 30 and inner surface 28 is preferably perpendicular to facial surface 64.

Figure 7:
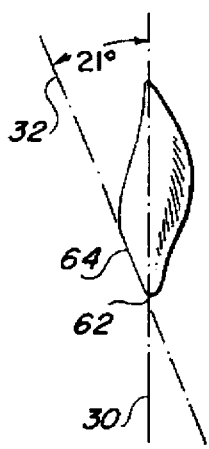
FIG. 7 is a side view of an upper cuspid tooth.

Referring now to FIG. 7, a profile of a representative upper cuspid tooth 70. Upper cuspid tooth 70 is also found in the upper (maxillary) jaw of a human mouth, and includes a biting surface 62, a facial surface 64, a longitudinal axis 30, and a line 32 tangent to facial surface 64. However, the angle made by longitudinal axis 30 and line 32 is about 28° in contrast to upper bicuspid tooth 60 which has an angle of 15°.

The present inventor has determined that the perfect working angle between respective surfaces 26 and 28 for upper cuspid tooth 70 is exactly equal to the 28° angle between axis 30 and line 32. With this angle, inner surface 26 is exactly perpendicular to longitudinal axis 30 and inner surface 28 is exactly perpendicular to facial surface 64.

Similar measurements of representative upper central, lower central, lower first bicuspid and lower molars yielded angles of 21°, 20°, 18° and 28° respectively between line 32 and axis 30. The present inventor has determined that the perfect working angle for respective surfaces 26 and 28 would equal the angle between axis 30 and line 32 for that tooth. Thus, to obtain the perfect angle for each tooth requires a set of instruments 10 which encompass all the possible tooth angles.

However, the use of an average angle of the respective tooth angles preferably in the range of about 15° to 28°, and most preferably about 22°, has been determined by the present inventor to be an optimum working angle when a single device is to be used for different teeth having different angles. Of course, an alternative embodiment using a set of instruments 10 angled for different teeth is certainly feasible and comes within the scope of the present invention. Such a set could include working instrument 10 designed for each tooth, or, alternatively, a set of instruments 10 having angles between respective inner surfaces 26 and 28 such as 17°, 20° and 24°. The 17° working angle is preferably suitable for use on upper bicuspid tooth 60, the lower molar or other teeth having angles between lines 32 and axis 30 that are less than 18°. The 20° working angle is preferably suitable for use on teeth such as the upper or lower central or other teeth having angles between 18° and 22°. The 24° working angle is preferably suitable for use on teeth such as upper cuspid 70 or lower first bicuspid or other teeth with angles greater than 22°.

The working angle of 22° is representative of an optimum design range, and approximates the angle between a first line tangent to the facial surface plane and a second line representing the longitudinal axis of most anterior teeth and most mandibular molar teeth. This working angle accommodates the average angle made between the longitudinal axis lines and the facial surface tangent lines of the maxillary posterior teeth (<22° angle) and the mandibular bicuspid teeth (>22°).

Figure 8:
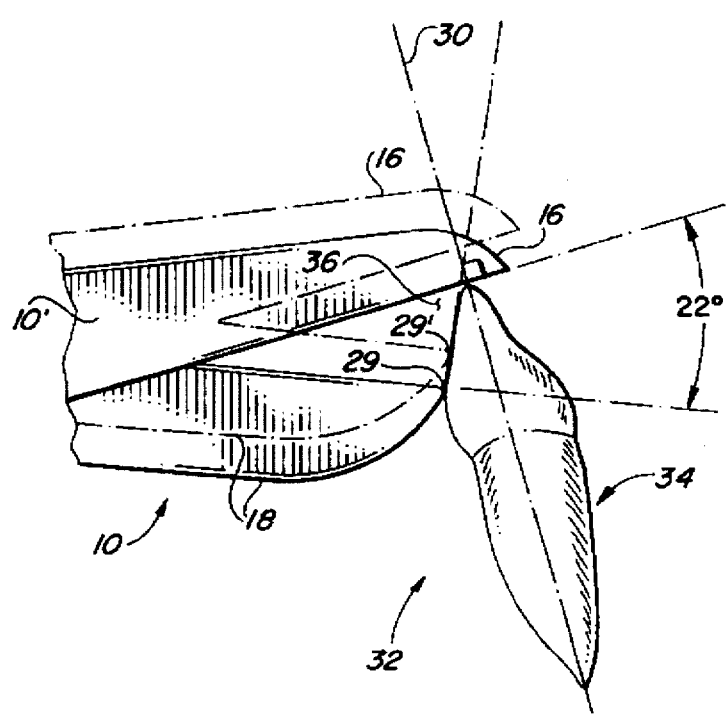
FIG. 8 is a side view of an exemplary embodiment of orthodontic pliers in accordance with the present invention.

The manner in which instrument 10 may be used to remove orthodontic appliances and cement, will now be described. Referring now to FIGS. 4, 5 and 8, instrument 10 is positioned with first jaw 16 perpendicular to a longitudinal axis 30 and cutting edge 29 of second jaw 18 is perpendicular to facial surface tangent line 32 at an area 36 of a tooth 34 where attachments are preferably adhered to tooth 34 by bonding materials such as cement. A user manipulates handles 20, 22 to cause jaw 18 to scrape at area 36 to either grasp the attachment for removal or to scrape the cement away.

If, however, attachments or bonding material are located at the position of cutting edge 29', then to function most efficiently and painlessly, jaw 18 and cutting edge 29 must move toward the biting surface as shown by instrument 10', where cutting edge 29' will engage the bonding material at a perpendicular angle to tangent line 32. At this point, if the desired 22° angle is maintained, first jaw 16' would not engage the biting surface of tooth 34.

In practice, first jaw 16 is maintained in its fulcrum position on the biting surface when instrument 10 is tipped forward in the hands of the user, thus keeping cutting edge 29 of jaw 18 on surface 32. However, this tipping or manipulation of instrument 10 creates a vector of force on the tooth as described earlier, in which first jaw 16 would tend to tip the tooth.

Thus, to minimize the tipping force, a sheath 40 in accordance with the present invention as seen in FIGS. 9 and 10 can be used over jaw 16. Sheath 40 includes a body portion having a cavity which releasably engages first jaw 16. A protective surface 42 of sheath 40 is positioned to correspond to inner surface 26 of first jaw 16.

Sheath 40 is preferably of plastic though other suitable materials will suggest themselves to those skilled in the art. Sheath 40 is designed to slope from the tip of jaw 16 toward pivot 24. Preferably, this slope is between about 5° to about 70°. However, the steeper angles are generally not practical because of tooth anatomy and the nature of the operation in which instrument 10 is opened and closed to remove residual pieces of cement and/or adhesive. Therefore, in practice, the angles preferably employed are about 5°–35°, most preferably about 15°.

It may be beneficial in many instances to have the angulated plastic sheath 40 on jaw 16, used in the design as shown in FIGS. 5 and 10, where jaw 18 is angulated rather than the design as shown in FIGS. 4 and 9 where jaw 16 is angulated. Thus, some angulation may be found in each jaw. The reason for the angulation of the sheath has been discussed previously. When less angulation of the plastic sheath 40 is used, it often becomes easier for the user to move jaw 16 about the biting surface of the tooth.

To hold plastic sheath 40 in place, inner surface 26 preferably includes a nub 44 corresponding to a depression 46 on sheath 40. Sheath 40 is preferably flexible enough to snap over first jaw 16 whereby nub 44 engages depression 46 to hold sheath 40 in place. Of course, many other suitable methods of attachment are available. Such techniques are well known to those skilled in the art and will not be further discussed herein.

Alternatively, inner surface 26 of instrument 10 could be shaped as described for plastic sheath 40. However, sheath 40 is preferably disposable which offers sanitary advantages as well. In addition, sheath 40 protects the biting surface from chipping or fracture during the procedure.

Sheath 40 can be configured with different thicknesses for different teeth. For example, on teeth with smaller angles, sheath 40 could be made with a gradually increasing thickness from pivot 24 to the tip of first jaw 16. In cases of teeth where the facial plane is nearly parallel to the longitudinal axis, sheath 40 could be used to eliminate or reduce the angle between jaws 16, 18.

As noted in the Background section, plastic buttons or "biting surface plastics" used on dental instruments are not easily removable or replaceable. In addition, strict OSHA regulations require high heat, autoclavability, or the ability to withstand prolonged chemical sterilization. The plastic buttons presently used are incapable or have great difficulty complying with such regulations.

In contrast, sheath 40 in accordance with the present invention is easily removable and replaceable with a new, unused and sterile sheath. Thus, sterilization is not necessary as sheath 40 is simply discarded after such use.

Another alternative in accordance with the present invention which reduces the tipping force is the employment of an angular addition to second jaw 18 as seen in FIG. 11. In accordance with this embodiment, a second cutting edge 29b is offset and angulated at approximately 30° to jaw 16 when jaws 16 and 18 are in the working position. Second cutting edge 29b allows instrument 10 to be maintained in the proper working position without the tipping described previously.

Cutting edges 29a and 29b can be oriented to parallel a tooth's facial surface tangent line. This embodiment is desirable for teeth whose facial surface is essentially flat. For other teeth, orientation of cutting edges 29a and 29b is dependent on the tooth geometry.

Referring now to FIG. 12, a top view of an alternate embodiment in accordance with the present invention for use in constricted spaces of the mouth has first jaw 16 disposed horizontally from the centerline of handles 20, 22 by an angle of between 45° and 90°, most preferably about 65°. This embodiment is particularly useful for use on teeth located in the posterior of the mouth and on some lingual surfaces. Disposing jaws 16 and 18 of instrument 10 as shown greatly improves the ability of the dentist to view the field of operation. Access to such teeth by straight instrument 10 illustrated in FIGS. 3, 4 and 5 is exceedingly difficult.

Referring to FIG. 13, an alternate embodiment in accordance with the present invention has first jaw 16 angled vertically toward second jaw 18 from the pivot point by about 3° to 10°, most preferably about 6° in addition to the horizontal displacement described in connection with FIG. 12. This alternate embodiment is useful because the occlusal surfaces of many teeth, and particularly the lower molars, are angulated toward the tongue (lingual). By angling first jaw 16 as described, the instrument compensates for the angulation of such teeth as the lower molars. When handles 20 and 22 are held comfortably in a horizontal working position, the user's field of vision is clear with respect to cutting edge 29. Without such angulation the plier must be rotated counter clockwise in the operator's hand obstructing vision and also making manipulation of the plier more difficult. Two pliers are necessary; the first for working in the lower left posterior area as shown in FIG. 13, the second a mirror image version of the first which is made for the lower right.

Referring again to FIG. 13, jaws 16 and 18 are divergent preferably at about 10° to 24° most preferably 18° when in the working position which is less than the previously most preferable 22° angle. The reduction is due to two factors. First, the instrument as illustrated has the working edge on the side of jaw 18 (rather than the end). When jaws 18 and 16 are closed, the forces created are more nearly parallel and opposite because they approach the tooth from approximately a 25° angle (90°–65°) rather than at a 90° angle as the previously described design illustrated. Secondly, many of the posterior teeth have less angular differences between the long axis and the line tangent to the facial surface and a reduction in angulation is therefore appropriate.

The above description is of preferred exemplary embodiments of the invention, as the invention is not limited to the specific forms shown. For example, the alternate embodiments illustrated in FIGS. 12 and 13 could utilize a different angle instead of the 65° bend which is illustrated. Other modifications may be made int he design and arrangement of the elements within the scope of the invention, as expressed in the appended claims.

That which is claimed is:

1. A dental instrument useful for removing attachments and cements from a surface of a tooth, the tooth further having a biting surface, a longitudinal axis, and a line tangent to the surface, the tangent line intersecting the longitudinal axis, the instrument comprising:

a first member having a first handle at one end thereof and a first jaw which is disposed at the opposite end of said first member, said first jaw including a first inner surface;

a second member having a second handle at one end thereof and a second jaw which is disposed at the opposite end of said second member, said second jaw including a second inner surface;

said first and second members being connected at a pivot mounted on a centerline of the instrument such that said first handle generally opposes said second handle and said first jaw generally opposes said second jaw, said first and second handles being manipulable in a working position to correspondingly cause said jaws to move in the working position;

said first jaw having a length greater than the length of said second jaw, the working position having the first inner surface engaged with the biting surface and the second inner surface engaged with the attachments and cements on the surface of the tooth; and one of the first and second inner surfaces being radially oriented with respect to said pivot where engaged in the working position and the other of the first and second inner surfaces being disposed at an acute angle where engaged in the working position with respect to the radially oriented inner surface.

2. The instrument according to claim 1 wherein the first jaw is longer than the second jaw by about the width of a tooth.

3. The instrument according to claim 2 wherein the acute angle in the working position is defined by the intersection of the longitudinal axis and the line tangent to the to the tooth's surface.

4. The instrument according to claim 2 wherein the acute angle is between about 10° to 40°.

5. The instrument according to claim 1 wherein the second jaw includes a cutting edge oriented parallel to the side of the tooth to be scraped.

6. The instrument according to claim 3 wherein the cutting edge is in the working position when separated by about four to ten millimeters from the inner surface of the first jaw.

7. The instrument according to claim 5 further comprising a second cutting edge of the second jaw, the second cutting edge being parallel to the side of the tooth.

8. The instrument according to claim 1 wherein the first jaw and the second jaw are horizontally disposed at an angle from the centerline of the instrument.

9. The instrument according to claim 8 wherein the angle of horizontal disposition is between about 45° and 90°.

10. The instrument according to claim 8 wherein the first jaw and the second jaw are further vertically disposed at an angle from the centerline of the instrument.

11. The instrument according to claim 1 further comprising a disposable sheath covering the first jaw, the sheath comprising:

a body portion defining a cavity for encompassing the first inner surface of the dental instrument, the body portion being releasably attached to the dental instrument; and a protective surface corresponding to the first inner surface for contact with teeth, the protective surface being disposed at an angle with respect to the first inner surface, the angle of disposition being sufficient to maintain the acute angle between the protective surface and the second inner surface at all working positions.

12. A disposable sheath for use in protecting teeth from contact with a first inner surface of a dental instrument useful for removing attachments and cements from a surface of a tooth, the tooth further having a biting surface, a longitudinal axis, and a line tangent to the surface, the tangent line intersecting the longitudinal axis, the instrument comprising a first member having a first handle at one end thereof and a first jaw which is disposed at the opposite end of said first member, said first jaw including the first inner surface, a second member having a second handle at one end thereof and a second jaw which is disposed at the opposite end of said second member, said second jaw including a second inner surface, said first and second members being connected at a pivot mounted on a centerline of the instrument such that said first handle generally opposes said second handle and said first jaw generally opposes said second jaw, said first and second handles being manipulable in a working position to correspondingly cause said jaws to move in the working position, said first jaw having a length greater than the length of said second jaw, the working position having the first inner surface engaged with the biting surface and the second inner surface engaged with the attachments and cements on the surface of the tooth, and one of the first and second inner surfaces being radially oriented with respect to said pivot where engaged in the working position and the other of the first and second inner surfaces being disposed at an acute angle where engaged in the working position with respect to the radially oriented inner surface, the sheath comprising:

- a body portion defining a cavity for encompassing the surface of the dental instrument, the body portion being releasably attached to the dental instrument; and
- a protective surface corresponding to the dental instrument surface for contact with teeth, the protective surface being disposed at an angle with respect to the first inner surface, the angle of disposition being sufficient to maintain the acute angle between the protective surface and the second inner surface at differing working positions.

13. The sheath of claim 12 wherein the body portion further defines a recess, the recess cooperating with a corresponding nub on the dental instrument to releasably attach the sheath to the dental instrument.

14. The sheath of claim 12 wherein the angle of disposition is about 15°.

* * * * *